US009717496B2

(12) United States Patent
Mandakolathur Vasudevan et al.

(10) Patent No.: US 9,717,496 B2
(45) Date of Patent: *Aug. 1, 2017

(54) SURGICAL STAPLING INSTRUMENT WITH LOCKING FEATURE TO LOCK ANVIL ACTUATOR

(71) Applicant: Ethicon Endo-Surgery, Inc., Cincinnati, OH (US)

(72) Inventors: Venkataramanan Mandakolathur Vasudevan, Cincinnati, OH (US); Edward G. Chekan, Chapel Hill, NC (US); Kevin D. Felder, Cincinnati, OH (US); Jerome R. Morgan, Cincinnati, OH (US); Carl J. Shurtleff, IV, Mason, OH (US); Johnny H. Alexander, III, West Chester, OH (US); John F. Cummings, Madeira, OH (US); Christopher C. Miller, Loveland, OH (US)

(73) Assignee: Ethicon LLC, Guaynabo, PR (US)

(*) Notice: Subject to any disclaimer, the term of this patent is extended or adjusted under 35 U.S.C. 154(b) by 0 days.

This patent is subject to a terminal disclaimer.

(21) Appl. No.: 14/944,387

(22) Filed: Nov. 18, 2015

(65) Prior Publication Data

US 2016/0066906 A1 Mar. 10, 2016

Related U.S. Application Data

(63) Continuation of application No. 13/328,402, filed on Dec. 16, 2011, now Pat. No. 9,220,505.

(51) Int. Cl.
*A61B 17/115* (2006.01)
*A61B 17/064* (2006.01)
(Continued)

(52) U.S. Cl.
CPC .......... *A61B 17/068* (2013.01); *A61B 17/115* (2013.01); *A61B 17/1155* (2013.01)

(58) Field of Classification Search
CPC ... A61B 17/115; A61B 17/064; A61B 17/068; A61B 17/0682; A61B 17/0686;
(Continued)

(56) References Cited

U.S. PATENT DOCUMENTS 4,907,591 A * 3/1990 Vasconcellos ....... A61B 17/115
227/175.1
5,074,454 A * 12/1991 Peters .............. A61B 17/07207
227/178.1
(Continued)

FOREIGN PATENT DOCUMENTS

CN 100457053 C 2/2009
CN 101843509 A 9/2010
(Continued)

OTHER PUBLICATIONS

International Search Report dated Feb. 8, 2013 for Application No. PCT/US2012/068861.
(Continued)

*Primary Examiner* — Andrew M Tecco
*Assistant Examiner* — Praachi M Pathak
(74) *Attorney, Agent, or Firm* — Frost Brown Todd LLC

(57) ABSTRACT

A surgical stapling instrument for performing a circular anastomosis comprises a stapling head assembly, an actuator handle assembly, a shaft assembly, a safety latch, and a locking member. The stapling head assembly includes an anvil that moves relative to a staple holder and a staple driver to drive staples from the staple holder into tissue and against the anvil. The actuator handle assembly has a first actuator that controls motion of the anvil and a second actuator that controls motion of the staple driver. The shaft
(Continued)

assembly couples the stapling head assembly to the actuator handle assembly. The safety latch prevents operation of the second actuator when the gap between the anvil and staple holder is outside a predetermined range. The locking member is configured to prevent adjustment of the anvil gap after the desired staple height has been set inside the predetermined range.

20 Claims, 13 Drawing Sheets

(51) Int. Cl.
*A61B 17/068* (2006.01)
*A61B 17/072* (2006.01)

(58) Field of Classification Search
CPC .......... A61B 17/07207; A61B 17/1155; A61B 17/072; A61B 2017/00685; A61B 2017/07257; A61B 2017/2837; A61B 2017/2927
USPC ...................................................... 227/175.2
See application file for complete search history.

(56) References Cited

U.S. PATENT DOCUMENTS

| | | | |
|---|---|---|---|
| 5,205,459 A | 4/1993 | Brinkerhoff et al. | |
| 5,271,543 A | 12/1993 | Grant et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A * | 9/1994 | Main | A61B 17/115 227/179.1 |
| 5,533,661 A | 7/1996 | Main et al. | |
| 6,050,472 A | 4/2000 | Shibata | |
| 8,684,247 B2 * | 4/2014 | Scirica | A61B 17/07207 227/175.1 |
| 8,733,611 B2 * | 5/2014 | Milliman | A61B 17/0686 227/175.2 |
| 9,220,505 B2 * | 12/2015 | Vasudevan | A61B 17/115 |
| 2009/0230170 A1 * | 9/2009 | Milliman | A61B 17/0686 227/176.1 |
| 2012/0080480 A1 * | 4/2012 | Woodard, Jr. | A61B 17/0643 227/176.1 |
| 2012/0080498 A1 * | 4/2012 | Shelton, IV | A61B 17/0643 227/178.1 |

FOREIGN PATENT DOCUMENTS

| | | |
|---|---|---|
| EP | 1520523 | 4/2005 |
| EP | 1563792 | 8/2005 |
| EP | 2233084 | 9/2010 |
| JP | H01-310653 A | 12/1989 |
| JP | H05-212041 A | 8/1993 |
| JP | 2010-221027 A | 10/2010 |

OTHER PUBLICATIONS

International Preliminary Report on Patentability dated Jun. 17, 2014 for Application No. PCT/US2012/068861.
Chinese Search Report dated Mar. 17, 2016 for Application No. CN 201280061805.6, 2 pgs.
Japanese Office Action dated Dec. 6, 2016 for Application No. JP 2014-547336, 5 pgs.

* cited by examiner

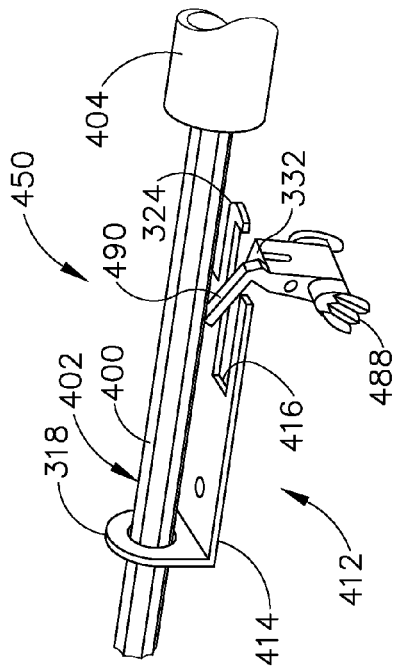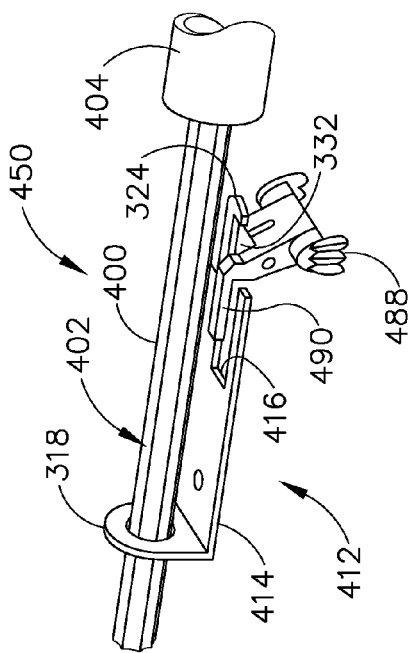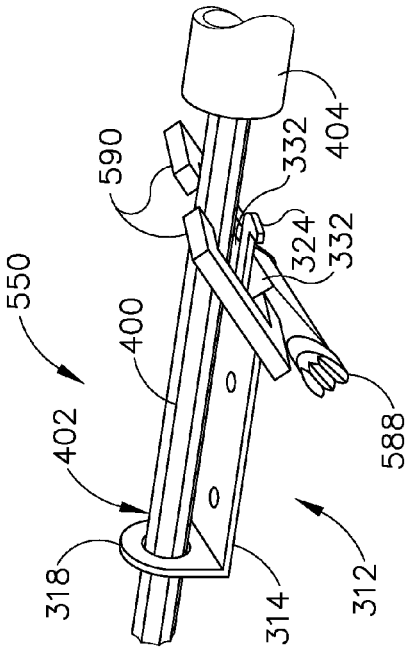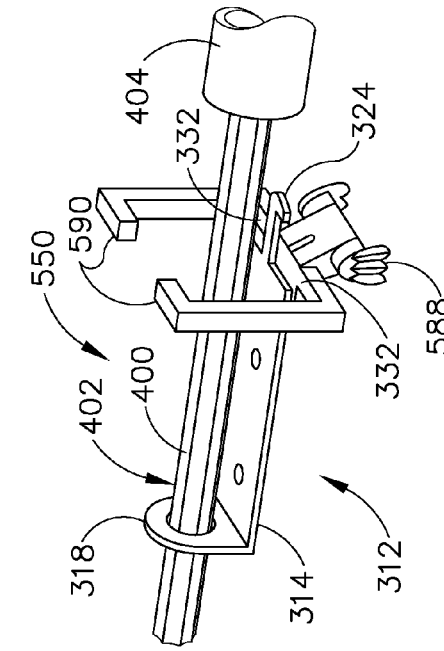
Fig. 8
Fig. 9
Fig. 10
Fig. 11

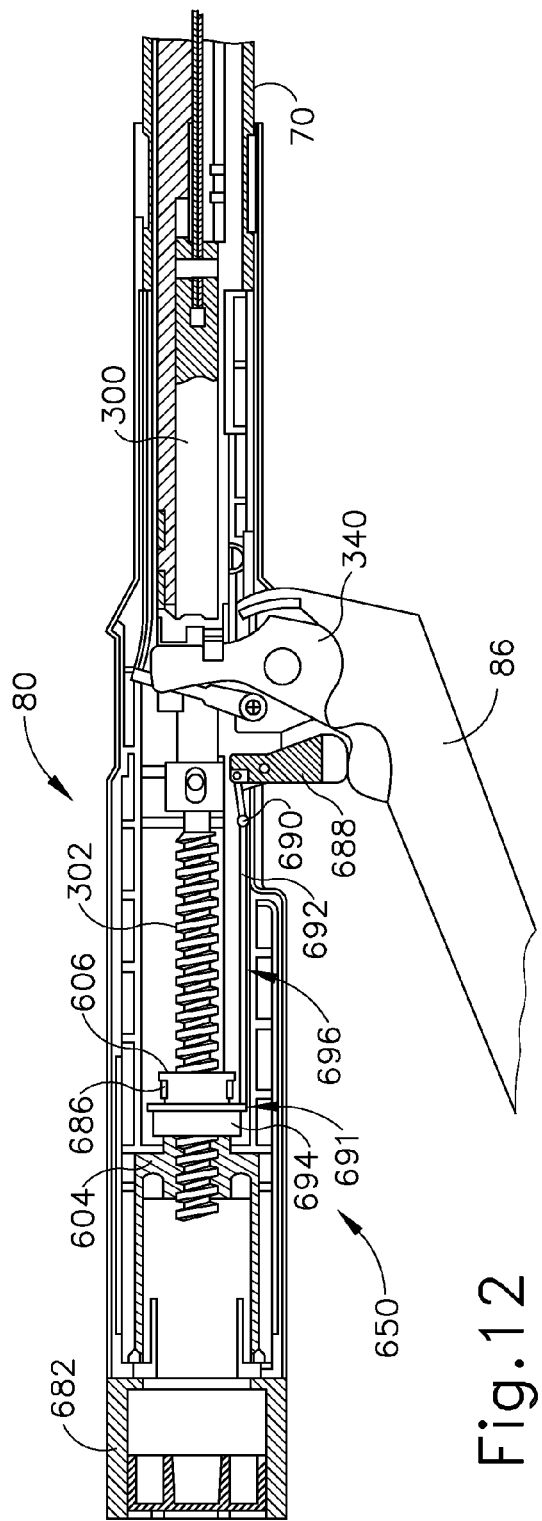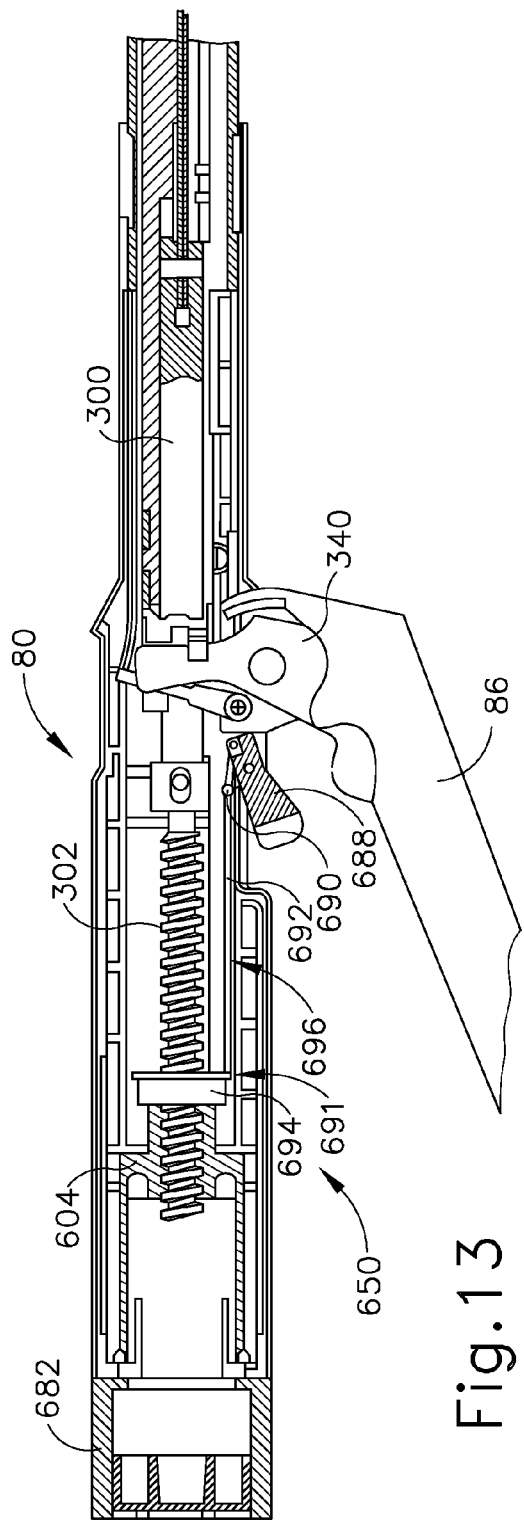

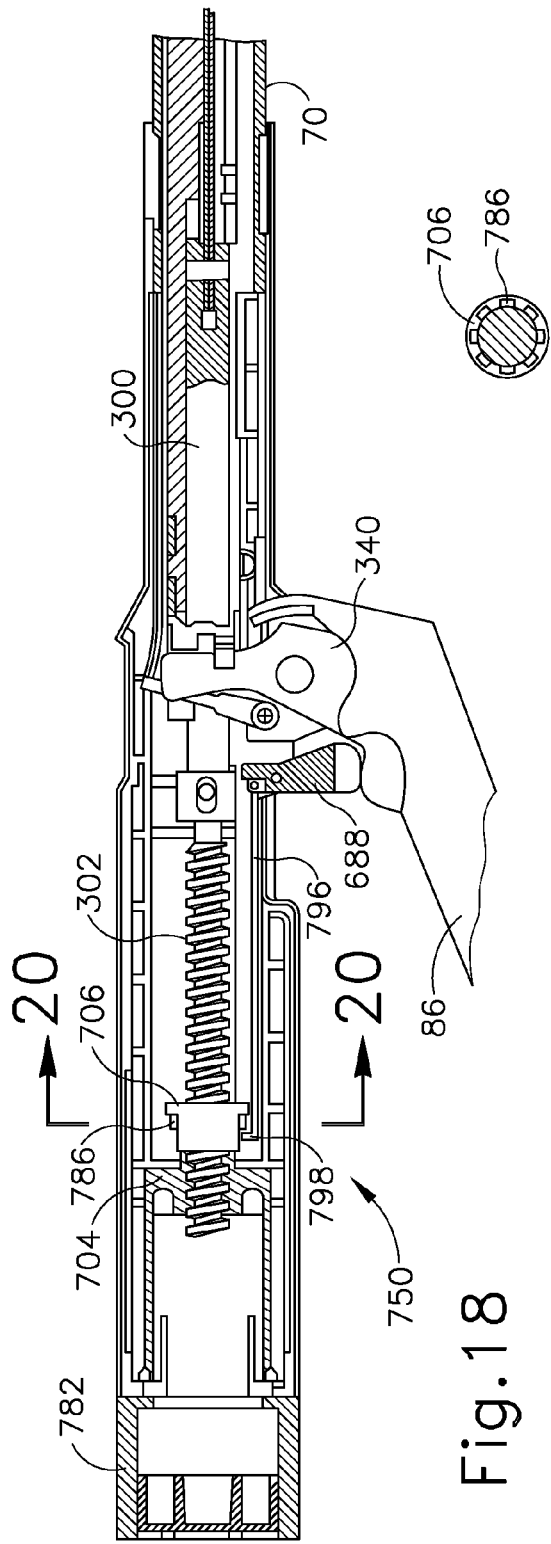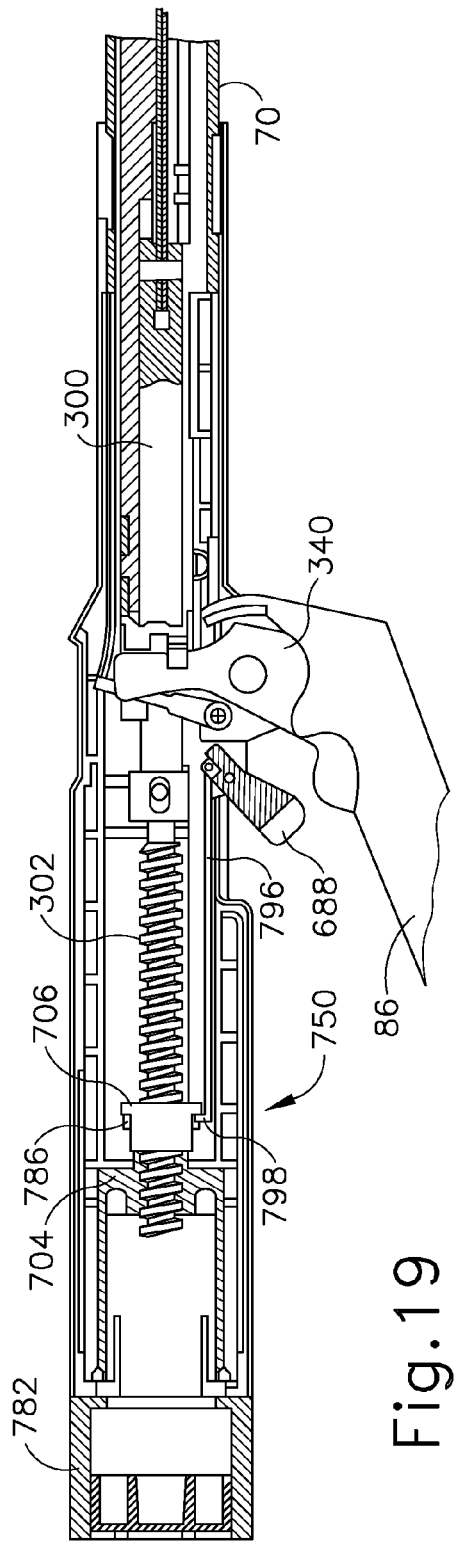

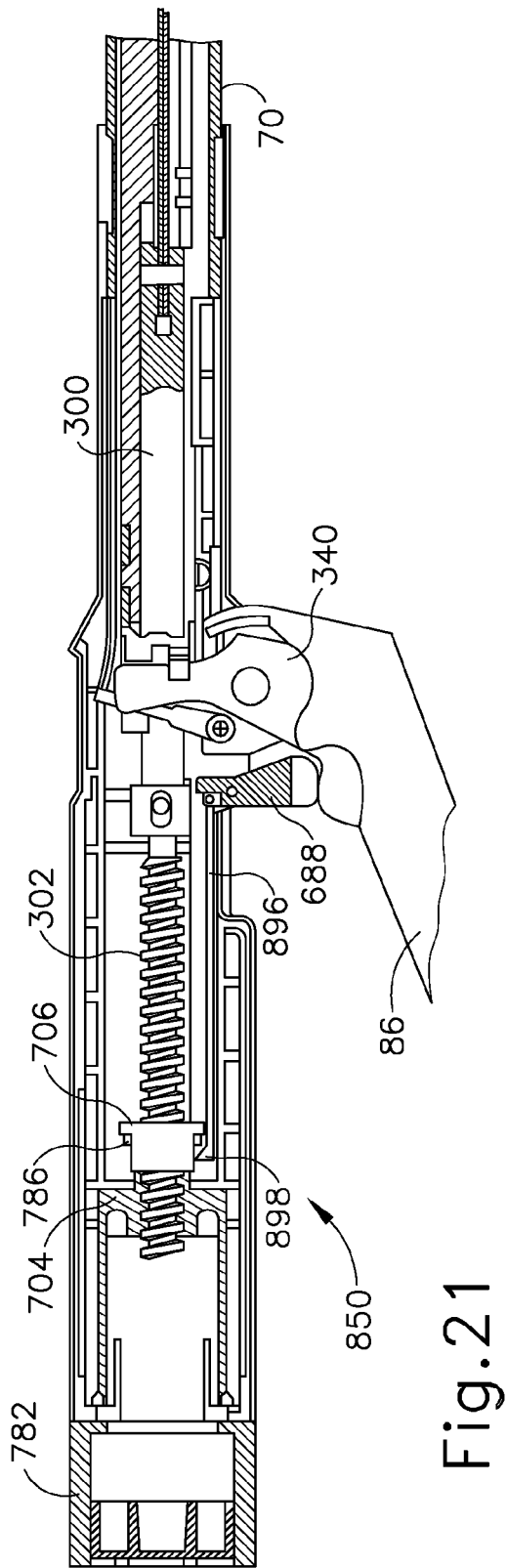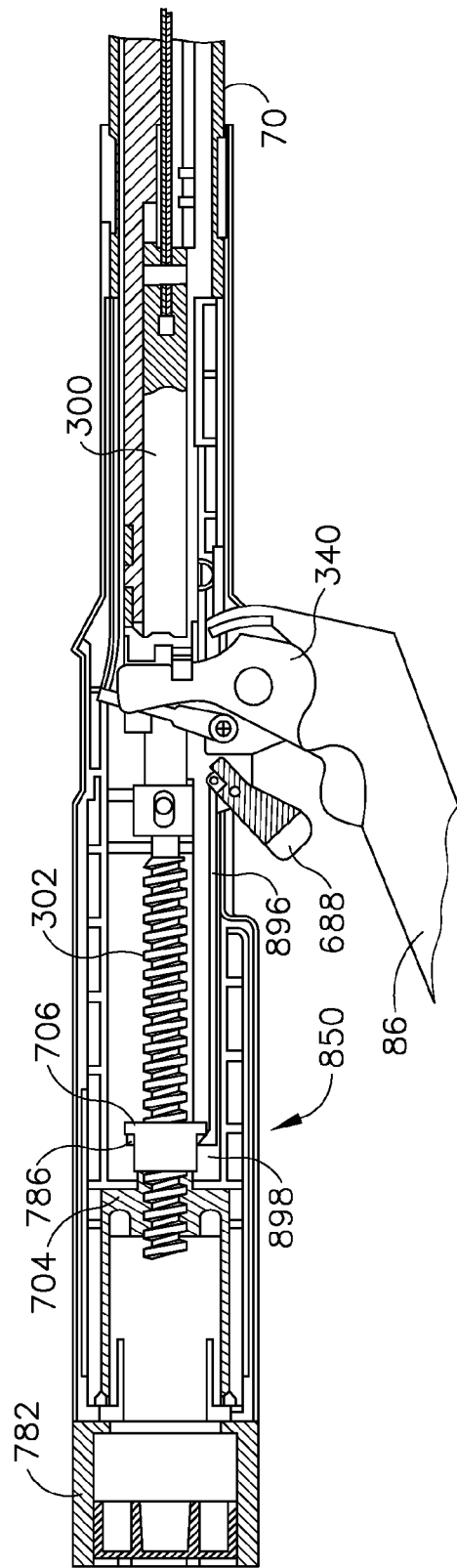

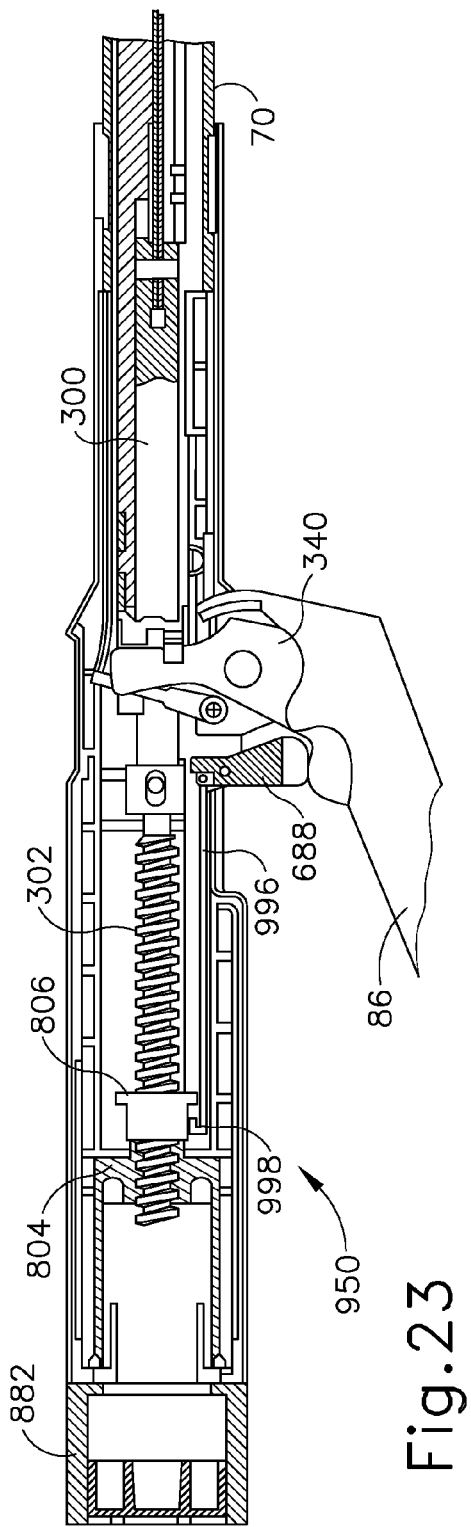
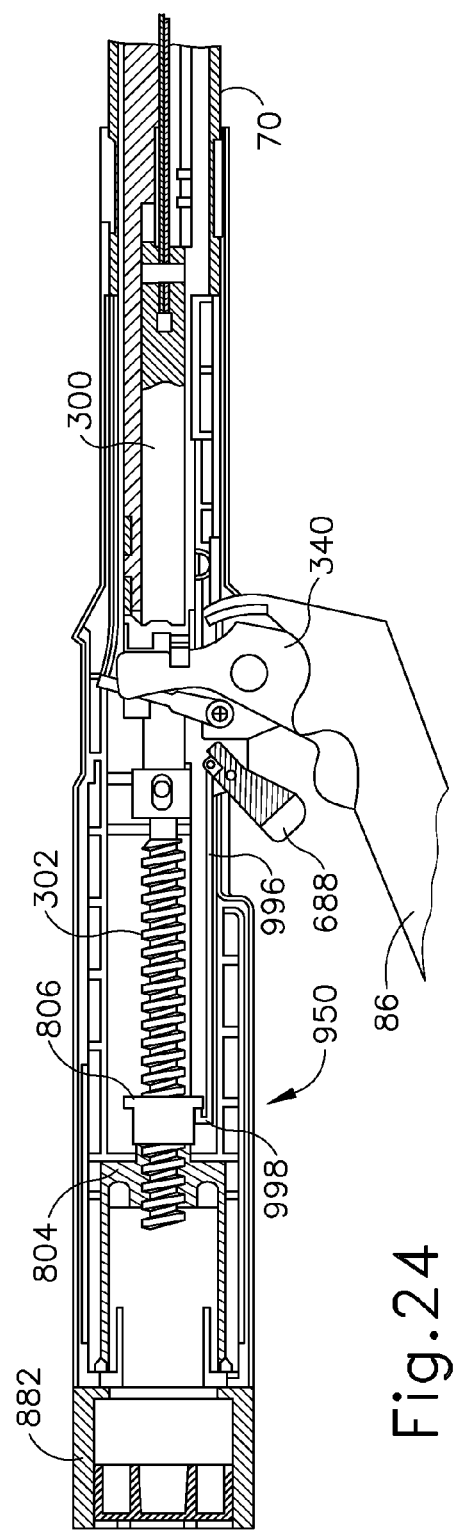

SURGICAL STAPLING INSTRUMENT WITH LOCKING FEATURE TO LOCK ANVIL ACTUATOR

This application is a continuation of U.S. application Ser. No. 13/328,402, filed Dec. 16, 2011, issued as U.S. Pat No. 9,220,505 on Dec. 29, 2015, entitled "Surgical Stapling Instrument with Locking Feature to Lock Anvil Actuator".

BACKGROUND

A variety of surgical stapling instruments perform circular anastomosis stapling operations. Examples of such devices and related concepts are disclosed in U.S. Pat. No. 5,205,459 entitled "Surgical Anastomosis Stapling Instrument," issued Apr. 27, 1993, the disclosure of which is incorporated by reference herein; U.S. Pat. No. 5,271,544 entitled "Surgical Anastomosis Stapling Instrument," issued Dec. 21, 1993, the disclosure of which is incorporated by reference herein; U.S. Pat. No. 5,275,322 entitled "Surgical Anastomosis Stapling Instrument," issued Jan. 4, 1994, the disclosure of which is incorporated by reference herein; U.S. Pat. No. 5,285,945 entitled "Surgical Anastomosis Stapling Instrument," issued Feb. 15, 1994, the disclosure of which is incorporated by reference herein; U.S. Pat. No. 5,292,053 entitled "Surgical Anastomosis Stapling Instrument," issued Mar. 8, 1994, the disclosure of which is incorporated by reference herein; U.S. Pat. No. 5,333,773 entitled "Sealing Means for Endoscopic Surgical Anastomosis Stapling Instrument," issued Aug. 2, 1994, the disclosure of which is incorporated by reference herein; U.S. Pat. No. 5,350,104 entitled "Sealing Means for Endoscopic Surgical Anastomosis Stapling Instrument," issued Sep. 27, 1994, the disclosure of which is incorporated by reference herein; and U.S. Pat. No. 5,533,661 entitled "Sealing Means for Endoscopic Surgical Anastomosis Stapling Instrument," issued Jul. 9, 1996, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of an exemplary safety release member in a position to lock the staple actuating lever;

FIG. 9 depicts a perspective view of the safety release member of FIG. 8, in a position to unlock the staple actuating lever and lock the adjusting knob;

FIG. 10 depicts a perspective view of another exemplary safety release member in a position to lock the staple actuating lever;

FIG. 11 depicts a perspective view of the safety release member of FIG. 10, in a position to unlock the staple actuating lever and lock the adjusting knob;

FIG. 12 depicts a longitudinal section view of an exemplary actuator handle assembly, illustrating a closure lockout member connected to a safety release member locking the staple actuating lever;

FIG. 13 depicts a longitudinal section view of the actuator handle assembly of FIG. 12, illustrating the safety release member locking the adjusting knob;

FIG. 18 depicts a longitudinal section view of an exemplary alternative actuator handle assembly, illustrating a linkage in a hook configuration connected to a safety release member locking the staple actuating lever;

FIG. 19 depicts a longitudinal section view of the actuator handle assembly of FIG. 18, illustrating the linkage locking the adjusting knob;

FIG. 20 depicts a cross section view of the adjusting knob taken along line 20-20 of FIG. 18;

FIG. 21 depicts a longitudinal section view of another exemplary actuator handle assembly illustrating a linkage in a wedge configuration connected to a safety release member locking the staple actuating lever;

FIG. 22 depicts a longitudinal section view of the actuator handle assembly of FIG. 21, illustrating the linkage locking the adjusting knob;

FIG. 23 depicts a longitudinal section view of another exemplary actuator handle assembly illustrating a linkage in a friction brake configuration connected to a safety release member locking the staple actuating lever; and FIG. 24 depicts a longitudinal section view of the actuator handle assembly of FIG. 23, illustrating the linkage locking the adjusting knob.

Figure 1:
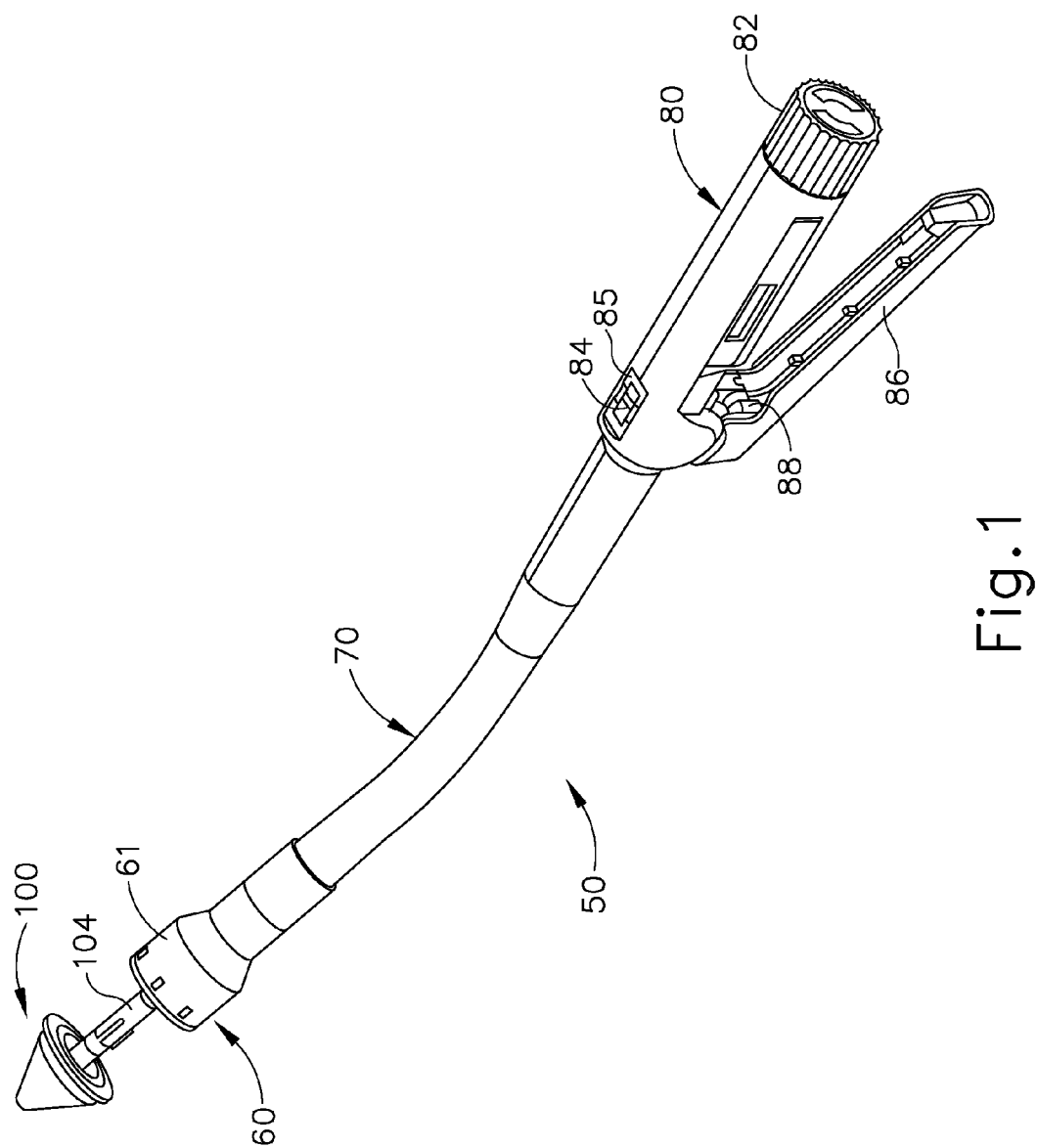
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Anastomosis Stapling Instrument

Referring to FIG. 1, the circular surgical anastomosis stapling instrument (50) of the present example includes a distal stapling head assembly (60) connected by a longitudinal support shaft assembly (70) to a proximal actuator handle assembly (80). The stapling instrument includes an anvil assembly (100) which is slidable longitudinally relative to a stapling head assembly (60). A rotatable adjusting knob (82) is provided at the proximal end of an actuator handle assembly (80) for adjusting the spacing between stapling head assembly (60) and anvil assembly (100). A movable indicator (84) is visible through a window (85) on top of handle assembly (80) to indicate the staple height selected by rotation of adjusting knob (82).

A staple actuating lever (86) is pivotally mounted on actuator handle assembly (80) for driving the surgical staples from stapling head assembly (60) when anvil assembly (100) is closed to provide the desired staple height. A pivotal safety latch (88) is mounted on handle assembly (80) for locking staple actuating lever (86) against movement to preclude actuation of stapling head assembly (60) when the anvil gap is outside of a predetermined range. Safety latch (88) is also configured to lock adjusting knob (82) when safety latch (88) is pivoted to allow operation of staple actuating lever (86). While several features of stapling instrument (50) will be described in detail below, it should be understood that stapling instrument (50) may also incorporate at least some of the teachings of U.S. Pat. No. 5,205,459 and/or any other reference(s) incorporated by reference herein. Other suitable components, features, and operabilities that may be incorporated into stapling instrument (50) will be apparent to those of ordinary skill in the art in view of the teachings herein.

A. Exemplary Stapling Head Assembly and Anvil Assembly

Figure 2:
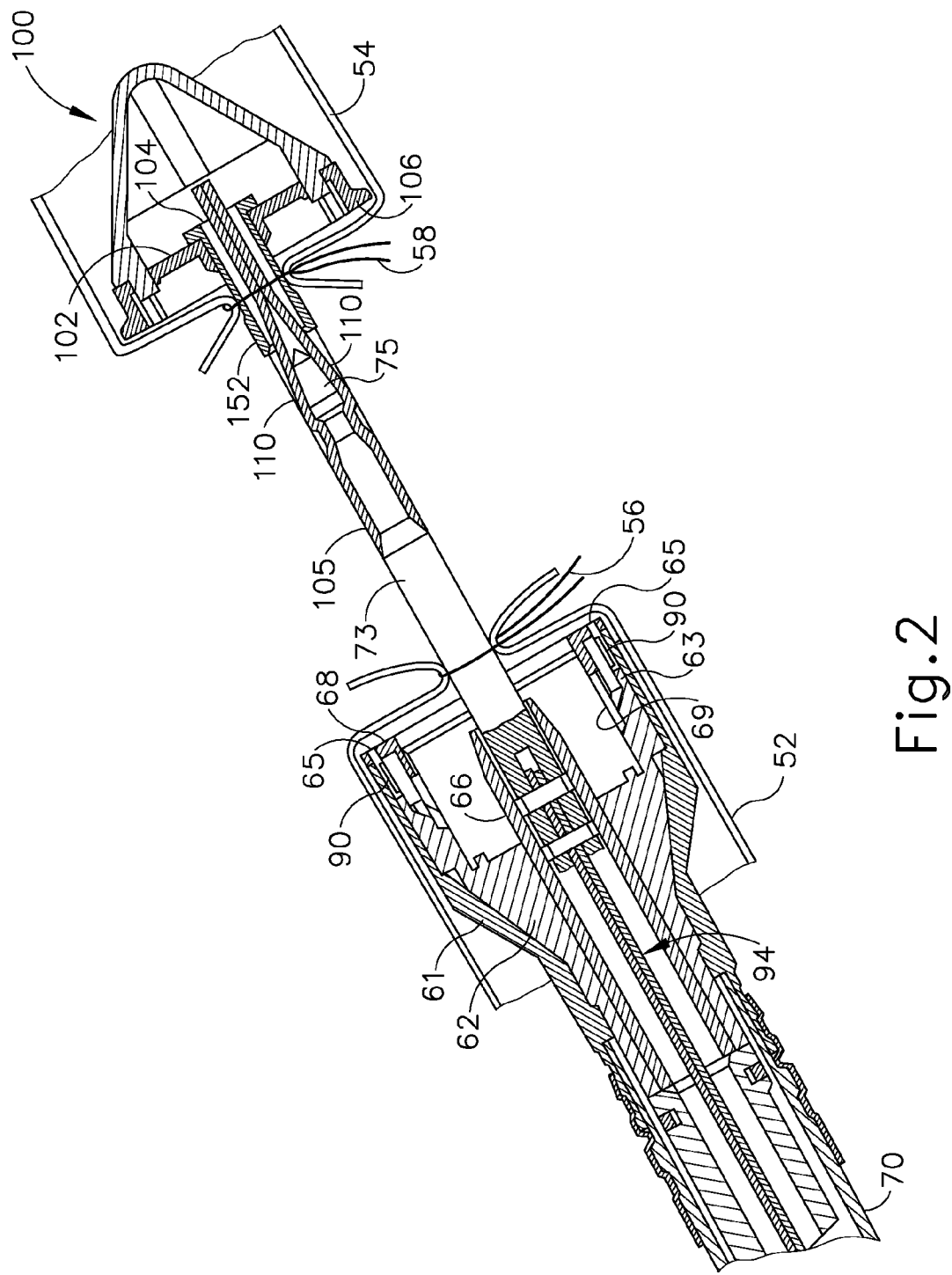
FIG. 2 depicts an enlarged longitudinal section view of a stapling head assembly of the instrument of FIG. 1, illustrating the anvil fully open.

Referring to FIG. 2, stapling head assembly (60) includes a tubular casing (61) that slidably receives a staple driver (62), which can be advanced and retracted by operation of actuator handle assembly (80). Staple driver (62) includes a plurality of fingers (63) for engaging and driving a plurality of staples (90) from a staple holder (68) mounted at the distal end of casing (61). Staple holder (68) includes a plurality of staple receiving slots (65) into which staples (90) are inserted. Also, staple driver (62) supports a circular knife or scalpel (69) which is advanced and retracted with staple driver (62).

Anvil assembly (100) includes a generally circular anvil (102) mounted on a hollow axially extending shaft (104), which is detachably secured to a trocar (73) slidably supported by stapling head assembly (60). Trocar (73) includes a pointed trocar tip (75) that is inserted into a hollow sleeve (105) at the proximal end of anvil shaft (104). In some alternative versions, the configurations of trocar (73) and hollow sleeve (105) are reversed such that trocar (73) is mounted to anvil assembly (100), with trocar tip (75) being inserted into a hollow sleeve (105) mounted to stapling head assembly (60) for operation. A pair of elongated, spring-like retainer clips (110) extends longitudinally along anvil shaft (104) for engaging trocar tip (75) when trocar (73) is inserted into anvil shaft (104). Trocar (73) is slidably received within a central support tube (66) formed on tubular casing (61) for longitudinal movement relative to staple holder (68) mounted at the distal end of casing (61). Staple receiving slots (65) in staple holder (68) are arranged in a circular array for receiving surgical staples (90). Staple receiving slots (65) are arranged in two closely spaced concentric annular rows. Anvil (102) includes an annular rim (106) having a plurality of staple forming grooves for forming staples (90) when driven against anvil (102).

Figure 3:
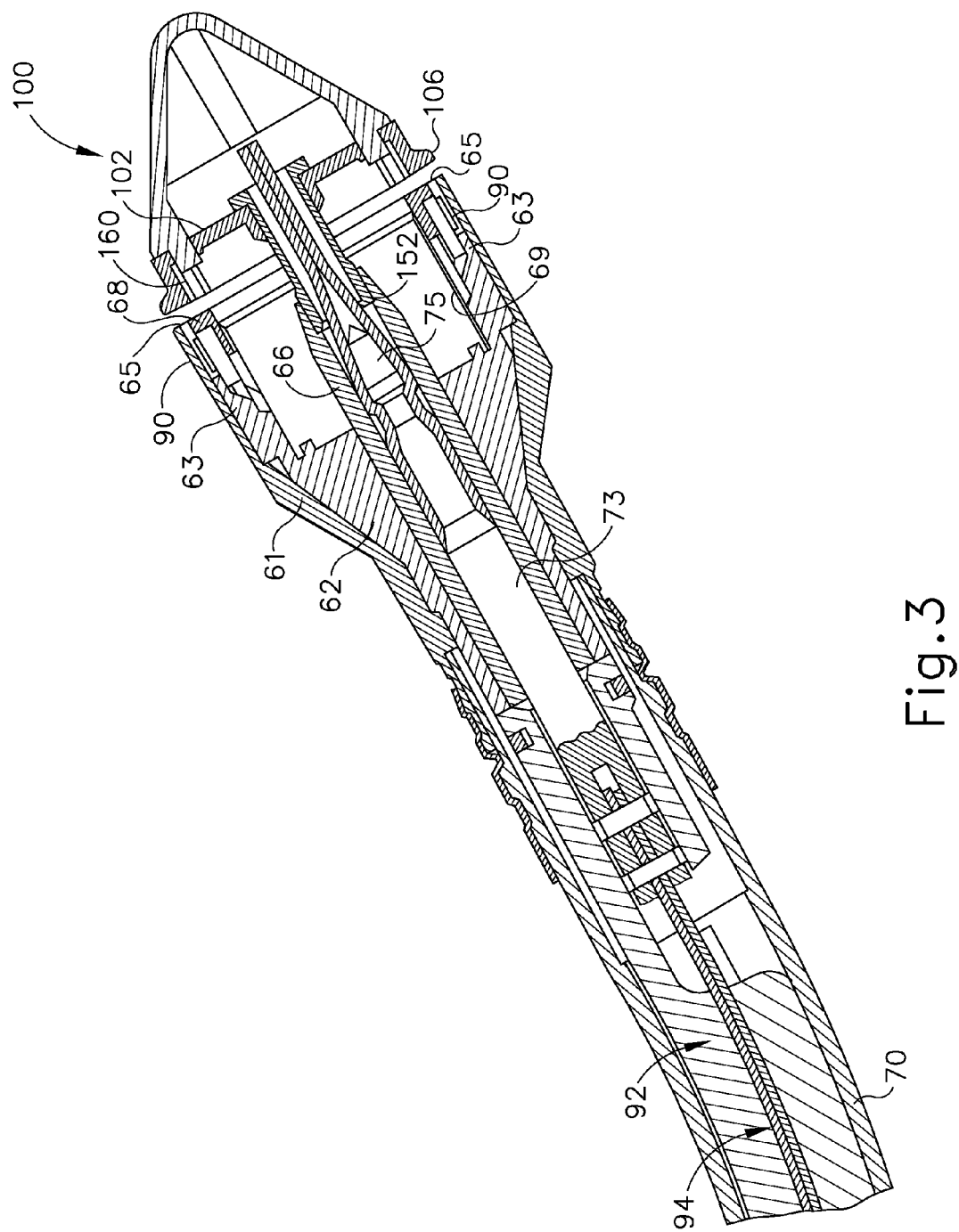
FIG. 3 depicts an enlarged longitudinal section view of the stapling head assembly of FIG. 2, illustrating the anvil in a closed position.

With stapling instrument (50) in its open position (FIG. 2), retainer clips (110) permit anvil assembly (100) to be attached to or detached from trocar (73) by pushing or pulling, respectively, on anvil assembly (100). With the stapling instrument in its closed position (FIG. 3), trocar (73) is retracted into central support tube (66) which restricts radial movement of retainer clips (110) to hold trocar tip (75) in place. As a result, anvil assembly (100) is locked to trocar (73) so that anvil (102) can resist the full firing force of the stapling instrument without disengagement of retainer clips (110) from trocar tip (75).

B. Exemplary Actuator Handle Assembly

Figure 5:
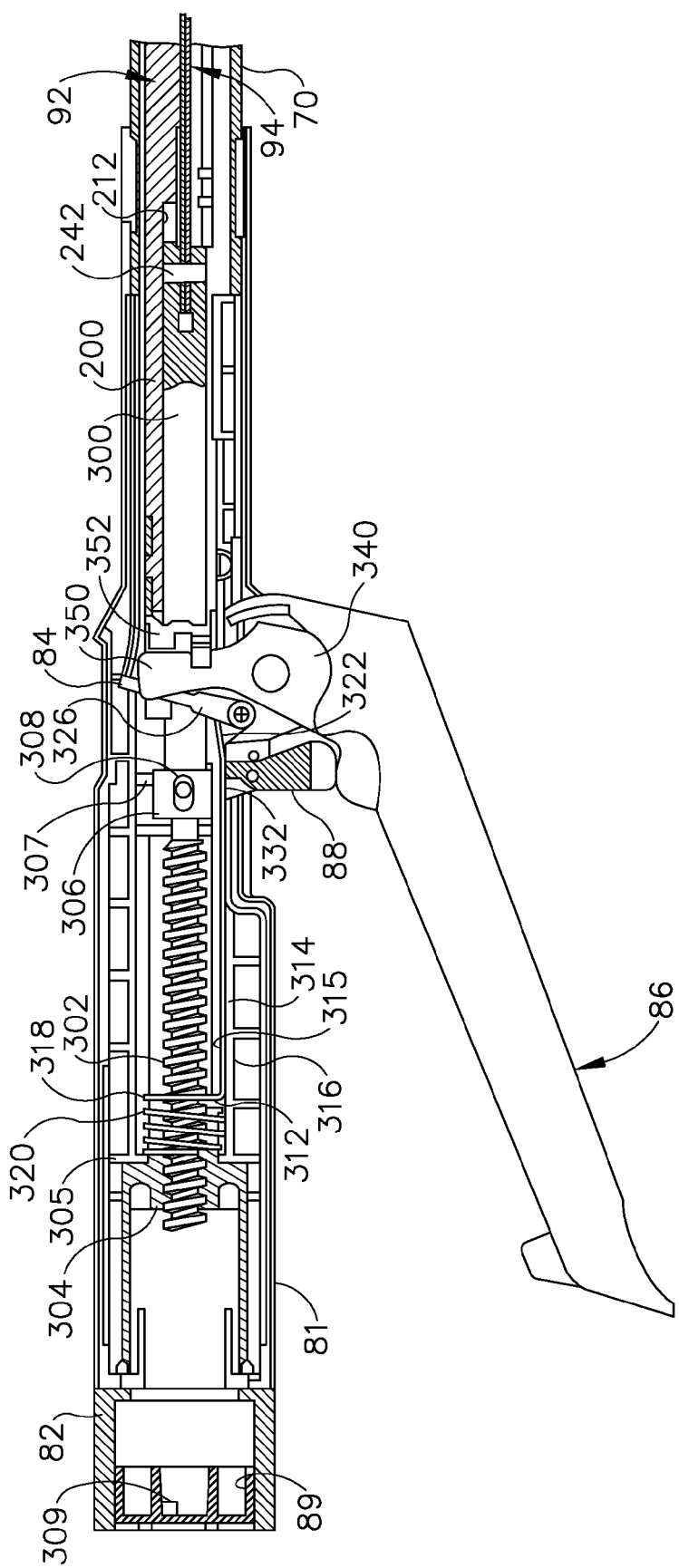
FIG. 5 depicts an enlarged longitudinal section view of an actuator handle assembly of the stapling instrument of FIG. 1, with the staple actuating lever in a locked position.

Referring to FIG. 5, actuator handle assembly (80) comprises a pair of elongated handle sections (81) that fit together to form a generally cylindrical handle. Stapling actuator lever (86) is pivotally mounted on handle sections (81). Control rod (300) is contained between handle sections (81) for longitudinal movement along actuator handle assembly (80). Adjusting knob (82) is rotatably supported by the proximal ends of handle sections (81) and is threadably engaged with an elongated threaded shank (302) at the proximal end of control rod (300). Threaded shank (302) and control rod (300) together form a unitary structure in this example. A cylindrical cap (89) is secured within the proximal end of hollow adjusting knob (82). Threaded shank (302) is threadably connected to an internally threaded sleeve (304) that is unitarily coupled with the distal end of adjusting knob (82). Threaded sleeve (304) is rotatably received in an annular wall (305) formed on each handle section (81) and rotates unitarily with adjusting knob (82). The distal end of control rod (300) is slidably received in an elongated groove (212) in proximal portion (200) of a compression member (92). Control rod (300) is connected at its distal end to a tension member (94) by a pin (242). Control rod (300) and threaded shank (302) are prevented from rotating within handle assembly (80). Thus, due to this and the threaded engagement between threaded sleeve (304) and threaded shank (302), threaded shank (302) and control rod (300) will translate relative to handle assembly (80) when adjusting knob (82) is rotated relative to handle assembly (80).

By rotating adjusting knob (82) in the counterclockwise direction, as viewed in FIG. 1, control rod (300) is advanced to move tension member (94) in the distal direction to open the gap between anvil assembly (100) and stapling head assembly (60). A stop (307) (FIG. 5) on one of handle sections (81) engages screw (308) to limit the distal movement of control rod (300). By rotating adjusting knob (82) in the opposite direction, i.e., clockwise, control rod (300) is retracted to move tension member (92) in the proximal direction to close the gap between anvil assembly (100) and stapling head assembly (60). A stop (309) on cap (89) limits the proximal movement of control rod (300).

C. Exemplary Locking Means for the Staple Actuating Lever

Actuator handle assembly (80) includes a safety release bracket (312) that is slidably supported on each of handle sections (81). Safety release bracket (312) includes an elongated rectangular plate (314) slidably received between a pair of longitudinal ribs (315) and (316) formed on each of handle sections (81) underneath threaded shank (302) of control rod (300). Threaded shank (302) extends through an upstanding flange (318) formed at the proximal end of rectangular plate (314). A coil spring (320) is interposed between flange (318) and annular wall (305) on each handle section (81) to normally bias flange (318) distally against rib (315). At the distal end of safety release bracket (312) is a distally projecting arm (322) which slopes upwardly and terminates at a laterally projecting finger (324) for controlling the movement of indicator (84).

Figure 6:
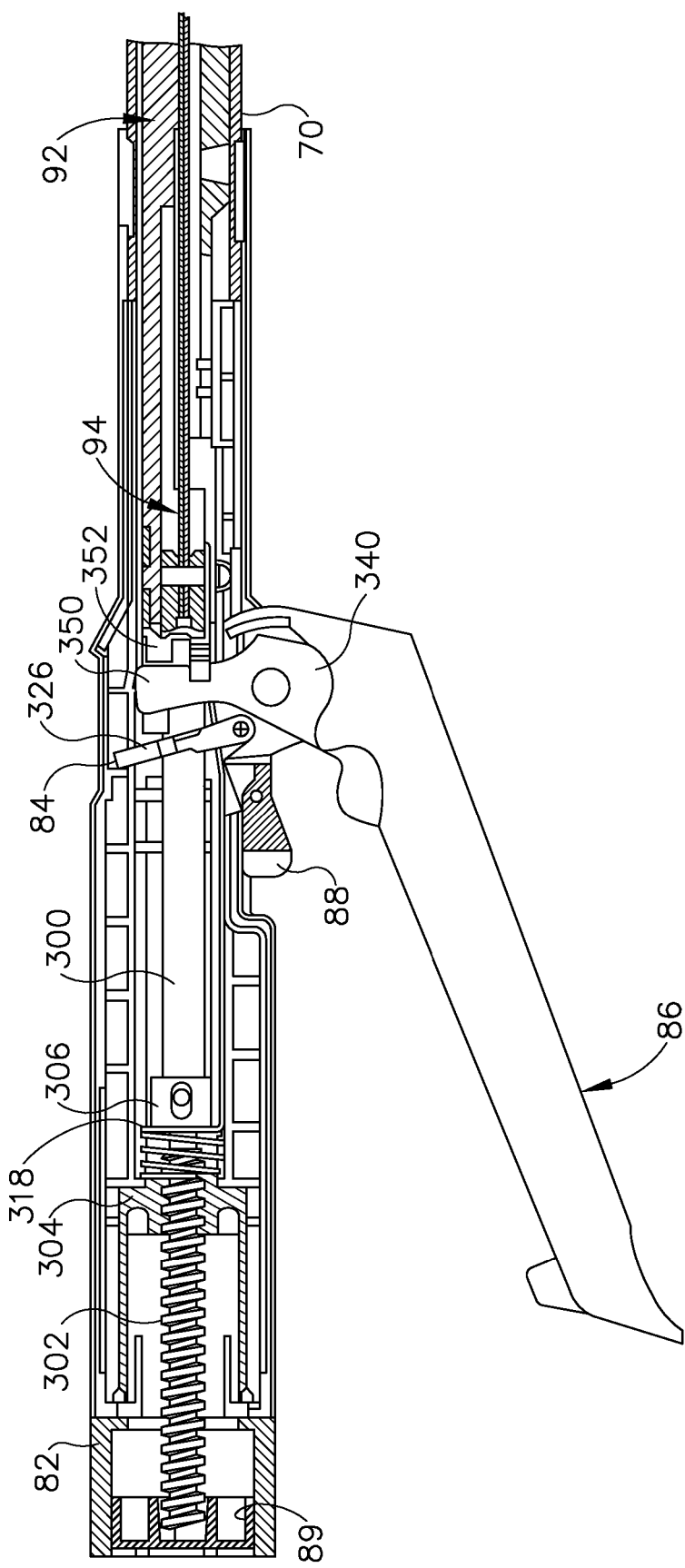
FIG. 6 depicts an enlarged longitudinal section view of the actuator handle assembly of FIG. 5, with the staple actuating lever in an unlocked position.

Anvil assembly (100) and actuator handle assembly (80) are shown fully open in FIGS. 2 and 5, respectively. With anvil assembly (100) fully open, safety release bracket (312) is biased distally by coil spring (320) to urge upstanding flange (318) against rib (315) with finger (324) advanced distally and disengaged from indicator lever (326). When control rod (300) is refracted, as shown in FIG. 6, clip (306) on control rod (300) is moved in a proximal direction to engage flange (318) and moves safety release bracket (312) in the proximal direction. Initially, as anvil assembly (100) begins to close, finger (324) on safety release bracket (312) remains disengaged from indicator lever (326). When the gap between anvil assembly (100) and stapling assembly (60) is adjusted into a predetermined range of the instrument, finger (324) engages and pivots indicator lever (326) to move indicator (84) proximally along a scale on window (85) to provide an indication of the selected staple height to be produced when the stapling instrument is fired.

Safety latch (88) is pivotally mounted beneath safety release bracket (312) by a pivot pin extending between handle sections (81). Safety latch (88) includes a ledge (332) which, in its latched position (FIG. 5), is disposed horizontally underneath safety release bracket (312). If the anvil gap is outside, i.e., above the predetermined range of the stapling instrument (FIGS. 2 and 5), rectangular plate (314) of safety release bracket (312) overlaps ledge (332) on safety latch (88) and prevents safety latch (88) from being disengaged from staple actuating lever (86). Safety latch (88) thus locks staple actuating lever (86) to the open position. On the other hand, when the anvil gap is within the predetermined range (FIGS. 3 and 6), safety release bracket (312) is retracted and ledge (332) on safety latch (88) is disengaged from rectangular plate (314) of safety release bracket (312). Safety latch (88) can then be pivoted upward (FIG. 6) to enable staple actuating lever (86) to be operated.

D. Exemplary Locking Means for the Adjusting Knob

Stapling instrument (50) may prevent motion of anvil assembly (100) after the anvil gap is adjusted to the desired staple height. For example, actuator handle assembly (80) may be modified so that adjusting knob (82) is prevented from rotating when safety latch (88) is pivoted upward to enable staple actuating lever (86) to be operated in the predetermined range. Examples described below include variations to actuator handle assembly (80) to lock adjusting knob (82) while staple actuating lever (86) is unlocked by safety latch (88). Other exemplary configurations will be apparent to those of ordinary skill in the art in view of the teachings herein.

1. Exemplary Adjusting Knob Locking Assembly Integral to the Safety Latch

Adjusting knob (82) may be selectively locked by a locking member that is integral to safety latch (88), such as a feature that moves unitarily with safety latch (88). Thus, some variations of safety latch (88) may engage a portion of actuating handle assembly (80) to prevent rotation of adjusting knob (82) when safety latch (88) is pivoted upward. One merely illustrative example is depicted in FIGS. 8-9, which show an adjusting knob locking assembly (450) that includes a knob extension rod (400), a safety latch (488), and a safety release bracket (412). Knob extension rod (400) is fixedly secured to adjusting knob (82) and extends distally therefrom. A threaded sleeve (404) having internal threading is fixedly secured to the distal end of knob extension rod (400), such that adjusting knob (82), knob extension rod (400), and threaded sleeve (404) all rotate together unitarily. Threaded sleeve (404) of this example is substantially similar to threaded sleeve (304) described above. In particular, threaded shank (302) of control rod (300) (not shown in FIGS. 8-9) is received in threaded sleeve (404), such that rotation of threaded sleeve (404) causes longitudinal translation of control rod (300). While threaded sleeve (304) of examples described above is located proximal to safety release bracket (312), threaded sleeve (404) of the present example is located distal to safety release bracket (412).

Knob extension rod (400) includes a flat sided region (402) proximal to threaded sleeve (404). In the present example, flat sided region (402) has an octagonal cross-section. In other versions, flat sided region (402) may include any polygon with any number of flat sides or regions and/or may be otherwise configured with a side surface that may be engaged by a feature of safety latch (488). Safety latch (488) is similar to safety latch (88) (FIG. 5), except that safety latch (488) of this example includes an integral arm (490) that extends from safety latch (488) so that arm (490) is capable of engaging knob extension rod (400) in the pivoted upward position (FIG. 9). Safety release bracket (412) is similar to safety release bracket (312) (FIG. 5), except that elongated rectangular plate (414) of safety release bracket (412) includes a slot (416) sized to allow arm (490) to pass within. In some other versions, plate (414) and arm (490) are configured such that arm (490) simply moves past an outer perimeter of plate (414) without having to pass through a slot or other feature in plate (414).

FIG. 8 shows adjusting knob locking assembly (450) in an unlocked position relative to adjusting knob (82). While safety latch (488) is in a downward position, actuating lever (86) is locked in place while knob extension rod (400) and threaded sleeve (404) are free to rotate upon movement of adjusting knob (82). Thus, control rod (300) may be longitudinally translated based on rotation of adjusting knob (82). Once safety latch (488) is pivoted upward (FIG. 9) to allow operation of staple actuating lever (86), arm (490) engages a flat sided region (402) of knob extension rod (400) to prevent rotation of knob extension rod (400). Arm (490) may engage a flat surface on the bottom, side, and/or top of knob extension rod (400). By preventing rotation of adjusting knob (82), knob extension rod (400), and threaded sleeve (404), the longitudinal position of control rod (300) is effectively locked in place. Thus, the anvil gap between anvil (102) and staple holder (68) is effectively locked in place when safety latch (488) is flipped upward to the position shown in FIG. 9.

In the present example, arm (490) is oriented substantially parallel to knob extension rod (400) in an unlocked position; and pivots to an orientation that is oblique relative to knob extension rod (400) in a locked position (FIGS. 8 and 9). In some other versions, arm (490) is oriented obliquely relative to knob extension rod (400) in an unlocked position; and pivots to an orientation substantially parallel to knob extension rod (400) in a locked position. Further, it should also be understood that a portion of adjusting knob (82) may contain one or more flat sides such that arm (490) selectively engages a flat surface of adjusting knob (82) to prevent rotation. Additional variations of the interface between arm (490) and knob extension rod (400) (e.g., an elastomeric friction brake, etc.) will be apparent to those of skill in the art in view of the teachings herein.

In an additional example, a portion of knob extension rod (400) may be configured with a smaller diameter, where the smaller diameter portion does not extend through the entire length of knob extension rod (400). As safety latch (488) is pivoted to an upward position, arm (490) may freely move past the outer diameter of the smaller diameter portion of knob extension rod (400), but arm (490) would be prevented from moving past the outer diameter of the larger diameter portion of knob extension rod (400). Thus, arm (490) would prevent rotation of knob extension rod (400) only when extension rod (400) is longitudinally positioned for engagement between arm (490) and the larger diameter portion of knob extension rod (400). Arm (490) would not prevent rotation of knob extension rod (400) when extension rod (400) is longitudinally positioned with the smaller diameter portion of knob extension rod (400) located by arm (490) since arm (490) could not engage such portion of knob extension rod (400).

FIGS. 10 and 11 show another example of an adjusting knob locking assembly (550). Adjusting knob locking assembly (550) of this example includes a knob extension rod (400), a safety latch (588) and a safety release bracket (312). Adjusting knob locking assembly (550) is similar to adjusting knob locking assembly (450) (FIGS. 8-9), except as otherwise described below. Safety latch (588) of adjusting locking assembly (550) is similar to safety latch (488) of adjusting knob locking assembly (450), except that safety latch (588) has a plurality of integral arms (590) that extend from safety latch (588). Arms (590) extend around safety release bracket (312) and are capable of engaging knob extension rod (400) on opposing flat surfaces of flat sided region (402) when safety latch (588) is in the pivoted upward position. Safety release bracket (312) of adjusting knob locking assembly (550) in this example is the same as safety release bracket (312) described above (e.g., with reference to FIG. 5).

FIG. 10 shows adjusting knob locking assembly (550) in an unlocked position relative to adjusting knob (82). While safety latch (588) is in this downward position, adjusting knob (82), knob extension rod (400), and threaded sleeve (404) are free to rotate while staple actuating lever (86) is locked in place. Once safety latch (588) is pivoted upward (FIG. 11) to allow operation of staple actuating lever (86), arms (590) engage opposing flat surfaces of knob extension rod (400) to prevent rotation of adjusting knob (82), knob extension rod (400), and threaded sleeve (404). By preventing rotation of adjusting knob (82), knob extension rod (400), and threaded sleeve (404), the longitudinal position of control rod (300) is effectively locked in place. Thus, the anvil gap between anvil (102) and staple holder (68) is effectively locked in place when safety latch (588) is flipped upward to the position shown in FIG. 11.

In the present example, a plurality of integral arms (590) are capable of engaging knob extension rod (400) on opposing flat surfaces of flat sided region (402) when safety latch (588) is in the pivoted upward position. However, additional variations of the interface between the integral arms (590) and knob extension rod (400), such as a friction brake, will be apparent to those of ordinary skill in the art in view of the teachings herein.

2. Exemplary Adjusting Knob Locking Assembly that Moves Longitudinally Relative to the Safety Latch Adjusting knob (82) and control rod (300) may be selectively locked by a feature that is liked to safety latch (88) instead of being a unitary feature of safety latch (88). Such a locking feature may translate in response to movement of safety latch (88), to thereby selectively lock adjusting knob (82) and control rod (300). Various examples of such features will be described in detail below, while other examples will be apparent to those of ordinary skill in the art in view of the teachings herein.

Figure 15:
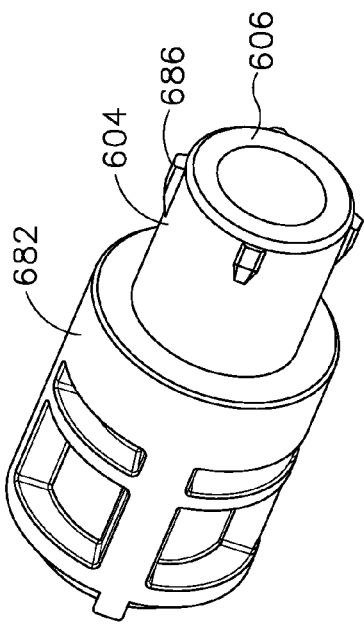
FIG. 15 depicts a perspective view of the adjusting knob of FIG. 12.
Figure 17:
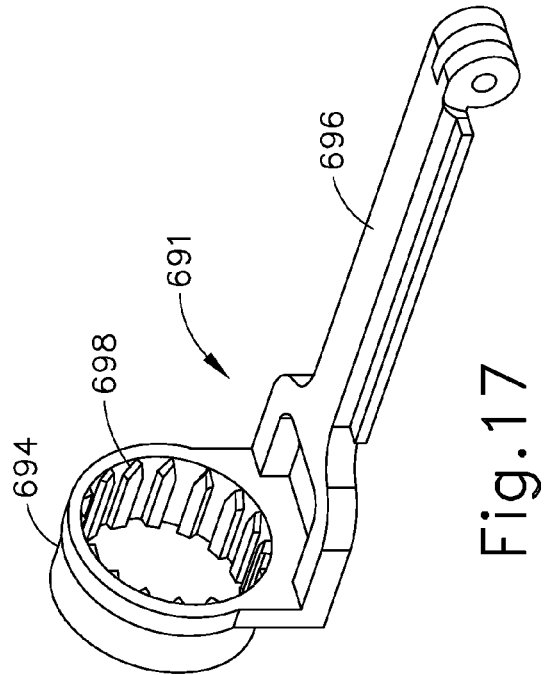
FIG. 17 depicts a perspective view of the closure lockout member of FIG. 13.
Figure 14:
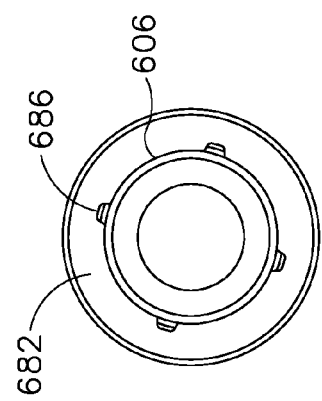
FIG. 14 depicts a front view of the adjusting knob of FIG. 12.
Figure 16:
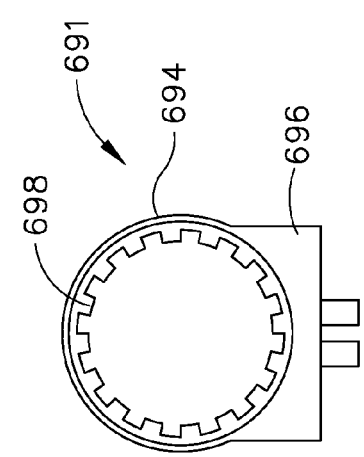
FIG. 16 depicts a front view of the closure lockout member of FIG. 13.

FIGS. 12-13 show an example of an adjusting knob locking assembly (650) that includes an adjusting knob (682), a closure lockout bracket (691), a safety latch link (690), and a safety latch (688). Adjusting knob (682) is similar to adjusting knob (82) (FIG. 5), except that threaded sleeve (604) at the distal end of adjusting knob (682) contains one or more outwardly extending exterior teeth (686) and a stop (606) (FIGS. 14 and 15). As shown in FIGS. 16 and 17, closure lockout bracket (691) includes a cylinder body (694), teeth (698) and a linkage bracket (696). Cylinder body (694) is coaxially aligned with threaded sleeve (604) and has a plurality of inwardly extending teeth (698). Teeth (698) are configured to selectively mesh with teeth (686) as will be described in greater detail below. Linkage bracket (696) extends from cylinder body (694) to connect closure lockout bracket (691) to safety latch link (690). Closure lockout bracket (691) is constrained to move only longitudinally within handle assembly (80).

Safety latch link (690) pivotally connects closure lockout bracket (691) to safety latch (688). Safety latch link (690) may comprise a bar, rod, or other such member. Safety latch (688) is similar to safety latch (88) (FIG. 5), except that safety latch (688) is capable of connecting to a linkage, such as safety latch link (690). The connection may be made at the top proximal end of safety latch (688) (FIG. 12), or any other area of safety latch (688). It should be understood that latch link (690) is configured to convert pivoting or rotational motion of safety latch (688) into longitudinal motion of closure lockout bracket (691). In particular, when safety latch (688) is pivoted from a first position (FIG. 12) to a second position (FIG. 13), safety latch link (690) pulls closure lockout bracket (691) distally. When safety latch (688) is pivoted from the second position (FIG. 13) back to the first position (FIG. 12), safety latch link (690) pushes closure lockout bracket (691) proximally.

Adjusting knob (682) and control rod (300) are locked when safety latch (688) is pivoted upward; and are unlocked when safety latch (688) is pivoted downward. In particular, when adjusting knob (682) is in an unlocked position (FIG. 12), closure lockout bracket (691) is in a proximal position such that teeth (698) are not engaged with teeth (686) on threaded sleeve (604) and adjusting knob (682) is free to rotate. When safety latch (688) is pivoted upward (FIG. 13), closure lockout bracket (691) moves distally to engage adjusting knob (682) to prevent rotation of adjusting knob (682) and translation of control rod (300). In the locked position, a portion of teeth (698) of cylinder body (694) mesh with at least a portion of teeth (686) on threaded sleeve (604). The diameters of cylinder body (694) and threaded sleeve (604) are sized so that teeth (686) of threaded sleeve (604) and teeth (698) of cylinder body (694) engage each other to prevent rotation of adjusting knob (682) to maintain the desired anvil gap and staple height when cylinder body (694) is advanced distally by safety latch (688). Teeth (686, 698) may be chamfered to guide cylinder body (694) over threaded sleeve (604). Safety latch (688) may be connected directly to closure lockout bracket (691) or safety latch (688) may be connected to closure lockout bracket (691) by one or more links, such as safety latch link (690). Adjusting knob locking assembly (650) may also be configured so that control rod (300) includes slots or teeth that engage closure lockout bracket (691) to prevent rotation of adjusting knob (682) and translation of control rod (300) when safety latch (688) is pivoted upward.

FIGS. 18-19 show another example of an adjusting knob locking assembly (750), which includes an adjusting knob (782), a linkage (796), a hook (798) and a safety latch (688). Adjusting knob (782) is similar to adjusting knob (682) (FIG. 12), except that threaded sleeve (704) at the distal end of adjusting knob (782) contains a plurality of outwardly extending teeth (786) and a stop (706), as best seen in FIG. 20. Linkage (796) comprises a bar, rod, or other member that connects safety latch (688) to hook (798). One or more linkages may be used to connect safety latch (688) to hook (798). Hook (798) extends vertically toward threaded sleeve (704). As safety latch (688) is pivoted upward to unlock actuating lever (86), linkage (796) moves distally and hook (798) engages teeth (786) of threaded sleeve (704) to prevent rotation of adjusting knob (682), thereby preventing translation of control rod (300).

FIGS. 21-22 show yet another example of an adjusting knob locking assembly (850), which includes an adjusting knob (782), a linkage (896), a wedge (898) and a safety latch (688). Adjusting knob locking assembly (850) is similar to adjusting knob locking assembly (750) (FIGS. 18 and 19), except that linkage (896) connects safety latch (688) to wedge (898). Wedge (898) extends vertically toward threaded sleeve (704). As safety latch (688) is pivoted upward to unlock actuating lever (86), linkage (896) moves distally and at least a portion of wedge (898) engages at least a portion of teeth (786) of threaded sleeve (704) to prevent rotation of adjusting knob (682), thereby preventing translation of control rod (300). A block or boss (not shown) may be used to prevent linkage (896) and wedge (898) from deflecting downwardly away from teeth (786) of threaded sleeve (704) when linkage (896) and wedge (898) are advanced distally.

FIGS. 23-24 show still another example of an adjusting knob locking assembly (950), includes an adjusting knob (882), a linkage (996), a friction brake (998) and a safety latch (688). Adjusting knob (882) is similar to adjusting knob (682) (FIG. 12), except that threaded sleeve (804) at the distal end of adjusting knob (782) contains a stop (806) without any teeth. Stop (806) is configured to have a larger diameter than threaded sleeve (804). Linkage (996) comprises a bar, rod, or other member that connects safety latch (688) to friction brake (998). Friction brake (998) is configured to selectively engage stop (806) on threaded sleeve (804). As safety latch (688) is pivoted upward to unlock actuating lever (86), linkage (996) moves distally and friction brake (998) engages stop (806) of threaded sleeve (804) to prevent rotation of adjusting knob (682) by the force of friction, thereby preventing translation of control rod (300). Various materials may be used on either or both of friction brake (998) or stop (806), such as an elastomer material.

It should be understood that a detent feature, over-center feature, and/or other type of selective retention feature may be incorporated to substantially hold safety latch (88, 488, 588, 688) in a pivoted upward position. Safety latch (88, 488, 588, 688) may also slide longitudinally instead of pivoting to selectively allow operation of staple actuating lever (86). Other suitable ways in which safety latch (88, 488, 588, 688) may be configured and operable will be apparent to those of ordinary skill in the art in view of the teachings herein.

II. Exemplary Operation of the Surgical Anastomosis Stapling Instrument

Surgical stapling instrument (50) can be used to perform an intraluminal anastomosis in which two sections of tissue are attached together by an array of staples. By way of example, stapling instrument (50) may be used in a procedure for joining a pair of hollow organ sections (e.g., in a patient's colon or other section of gastro-intestinal tract) end to end with a plurality of surgical staples arranged in a circular array around a hollow lumen between the organ sections. In preparation for the anastomosis, purse string sutures are placed in the hollow organs to be anastomosed. For example, as shown in FIG. 2, two tubular tissue sections (52) and (54) are prepared by threading purse string sutures (56) and (58), respectively, into the tissue in purse string fashion adjacent to the open ends of tubular tissue sections (52) and (54).

If the surgical procedure is performed using a double purse string suturing technique, stapling instrument (50) is inserted into first tubular tissue section (52), e.g., by insertion into the anal opening of the patient, with anvil assembly (100) attached to stapling head assembly (60) and completely closed. Prior to insertion of stapling instrument (50) into the patient, adjusting knob (82) is rotated clockwise to retract trocar (73) into support tube (66) and to clamp anvil (102) against staple holder (68). Stapling head assembly (60) is positioned adjacent to purse stringed end of tubular tissue section (52). Next, adjusting knob (82) is rotated clockwise to advance control rod (300) and tension member (92) until trocar (73) is fully advanced to move anvil assembly (100) to its fully open position (FIG. 2). With trocar (73) fully advanced, the purse stringed end of tubular tissue section (52) is drawn together about cylindrical trocar body (130) by pulling and tightening purse string suture (56). The purse stringed tissue is drawn against cylindrical trocar body (130) and purse string suture (56) is tied to hold the tissue against trocar body (130).

Anvil assembly (100) is inserted into the purse stringed end of the tubular tissue section (54) and the tissue is drawn together about anvil shaft (104) by pulling and tightening purse string suture (58). The purse stringed tissue is pulled against anvil shaft (104) in tying notch (158) distally adjacent to raised circumferential section (152) on anvil shaft (104) and purse stringed suture (58) is tied together. If desired, anvil assembly (100) may be detached from trocar (73) to facilitate the insertion of anvil assembly (100) into tubular tissue section (54). After the purse stringed end of tubular tissue section (54) is tied against anvil shaft (104) by purse string suture (58), anvil assembly (100) is re-attached to trocar (73).

After the purse stringed ends of tubular tissue sections (52) and (54) are tied, adjusting knob (82) is rotated clockwise to retract trocar (73) into support tube (66) to move anvil (102) toward staple holder (68). As trocar (73) is retracted, trocar body (130) slides through the purse stringed end of tissue section (52) in the proximal direction to pull anvil shaft (104) through the purse stringed tissue into support tube (66). Stapling instrument (50) eventually reaches the configuration shown in FIG. 3. Actuator handle assembly (80) remains in the fully advanced or open configuration shown in FIG. 5 during this transition.

Figure 4:
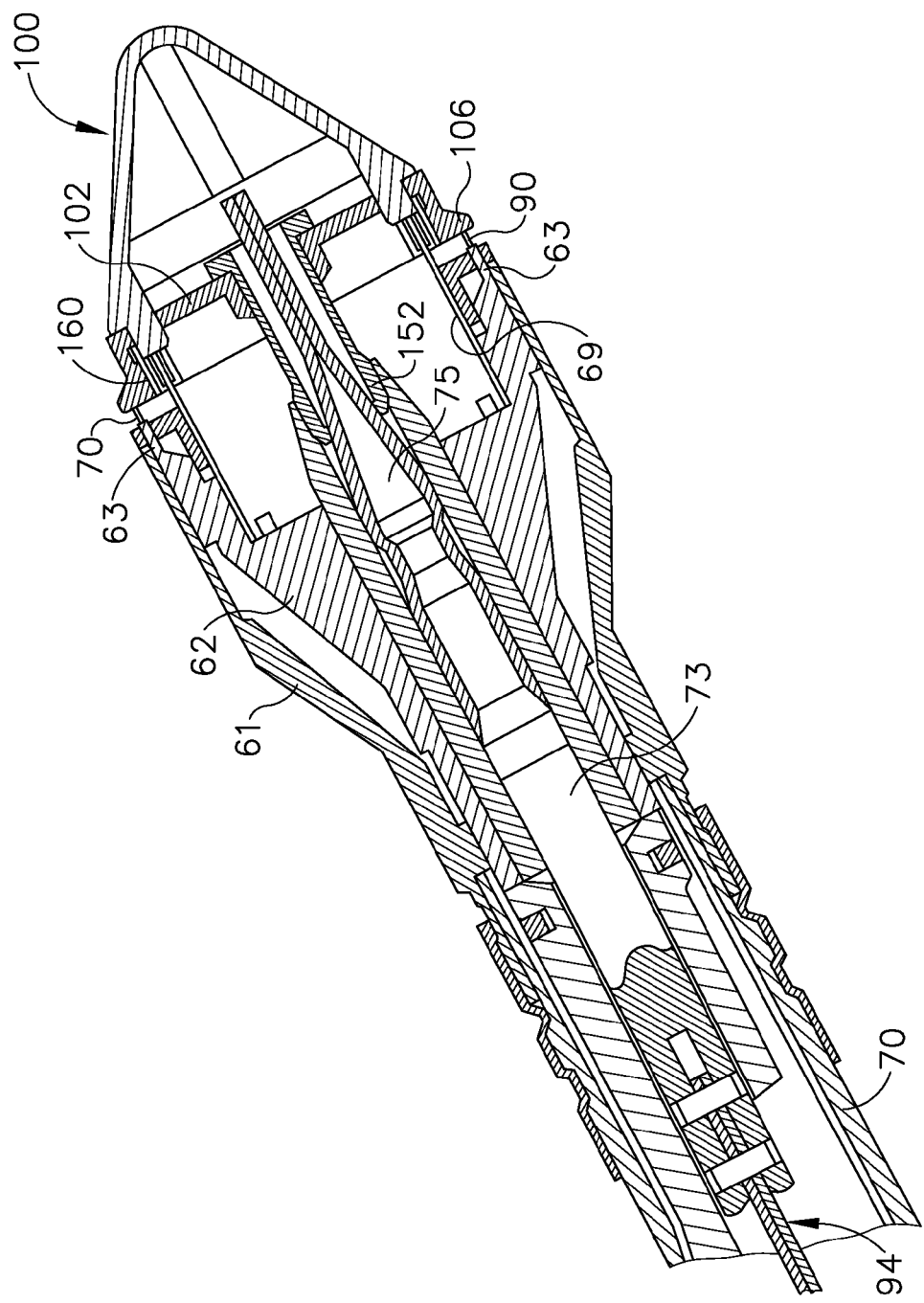
FIG. 4 depicts an enlarged longitudinal section view of the stapling head assembly of FIG. 2, illustrating the staple driver in a fired position.
Figure 7:
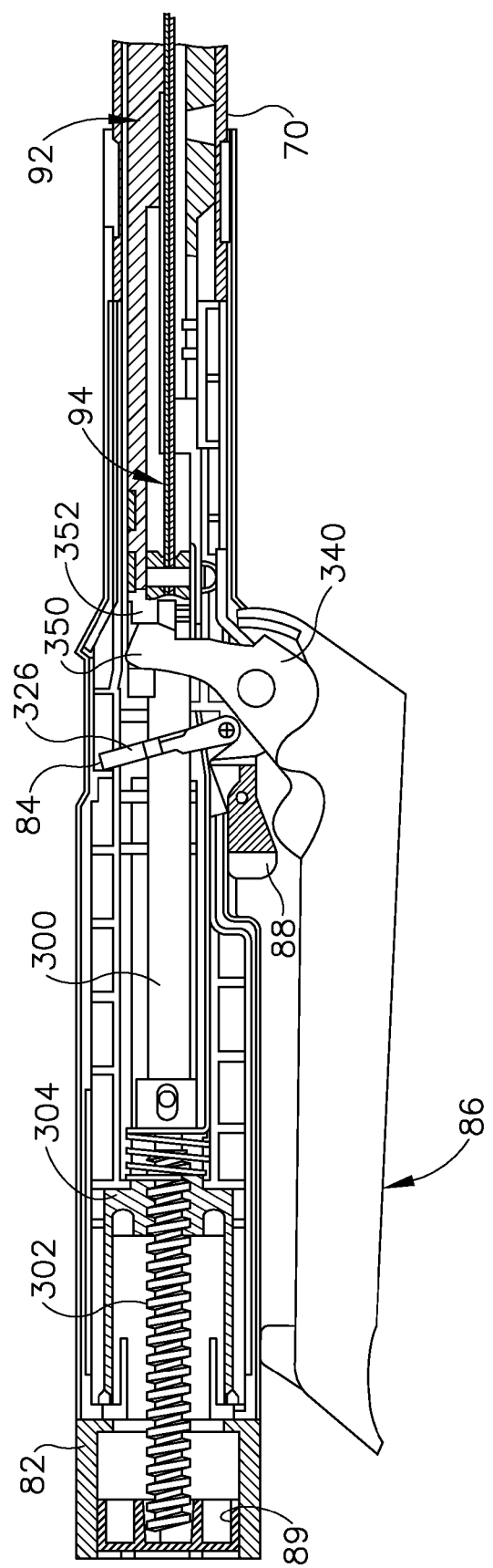
FIG. 7 depicts an enlarged longitudinal section view of the actuator handle assembly of FIG. 5, in a fired position.

When the gap between anvil (102) and staple holder (68) is set to produce a desired staple height within the operating range of stapling instrument (50), safety latch (88, 488, 588, 688) is pivoted upward (FIGS. 6, 9, 11, 13, 19, 22 and 24) to disengage staple actuating lever (86). In the pivoted position, safety latch (88, 488, 588, 688) engages either control rod (300), knob extension rod (400), or adjusting knob (82, 682, 782, 882) to prevent rotation of adjusting knob (82, 682, 782, 882) and to thereby maintain the selected staple height. Stapling instrument (50) is fired by grasping and pivoting staple actuating lever (86) clockwise, as viewed in FIG. 7, to move staple actuating lever (86) to its fired position. As a result, actuator fingers (350) on trigger arm (340) drive firing clip (352) in the distal direction to advance compression member (92) longitudinally along shaft assembly (70). Compression member (92) advances staple driver (62) to move driver fingers (63) distally in staple receiving slots (65) to engage staples (90). Compression member (92) transmits the required motion and compressive forces from trigger arm (340) to staple driver (62) to drive staples (90) from staple holder (68) into the tissue and against anvil (102). Also, circular knife (69) is advanced by staple driver (62) to cut the tissue against backup washer (160). As shown in FIG. 4, circular knife (69) splits backup washer (160) into two annular sections. Staples (90) join the ends of tissue sections (52) and (54) with a fluid tight seal formed by concentric annular rows of staples (90). Circular knife (69) cuts away excess tissue within the anastomosis near the stapled region. The severed excess tissue may be trapped within stapling head assembly (60) (e.g., between the interior of circular knife and the exterior of the assembly of trocar (73) and anvil shaft (104).

After the stapling and cutting of the tissue is completed, staple actuating lever (86) is biased by spring (346) to its fully open position (FIG. 6). Actuator fingers (350) of trigger arm (340) pivot counterclockwise, as viewed in FIG. 6, to move firing clip (352) and compression member (92) in the proximal direction. As a result, staple driver (62), which is connected by locator fingers (230) to compression member (92), and circular knife (69) are retracted into stapling head assembly (60). In case of entrapment of staples, tissue or other debris between staple holder (68) and driver fingers (63), the retraction of staple driver (62) frees stapling head assembly (60) from the tissue before stapling instrument (50) is withdrawn from the patient. If a high force is required, staple actuating lever (86) can be returned manually to its fully advanced position to retract staple driver (62).

Next, safety latch (88, 488, 588, 688) is pivoted downward, either manually or automatically in conjunction with firing stapling instrument (50). When safety latch (88, 488, 588, 688) is pivoted downward, staple actuating lever (86) is locked and adjusting knob (82, 682, 782, 882) is disengaged from safety latch (88, 488, 588, 688) so that adjusting knob (82, 682, 782, 882) may freely rotate. The stapled tissue between anvil (102) and staple holder (68) is released by rotating adjusting knob (82) counterclockwise to advance anvil assembly (100) away from stapling head assembly (60). Anvil (102) is moved through the lumen by manipulating the stapled tissue in a suitable manner to slip the anvil through the stapled lumen. Then, stapling instrument (50) is withdrawn from the patient leaving behind the stapled lumen between tubular tissue sections (52) and (54).

III. Miscellaneous

The examples described above include various structures for selectively preventing rotation of adjusting knob (82), to thereby selectively prevent translation of control rod (300), to effectively lock/hold an anvil gap during actuation of staple actuating lever (86). It should be understood that it may be possible to selectively prevent translation of control rod (300), in response to movement of safety latch (88, 488, 588, 688), without necessary preventing adjusting knob (82) from rotating. By way of example only, a clutch feature (not shown) may couple adjusting knob (82) with threaded sleeve (304), and a safety latch (88) may selectively engage/disengage the clutch feature. For instance, when safety latch (88) is in a position to lock staple actuating lever (86), the clutch feature may provide unitary rotation of adjusting knob (82) and threaded sleeve (304). When safety latch (88) is moved to a position to unlock staple actuating lever (86), this may cause the clutch feature to disengage adjusting knob (82) from threaded sleeve (304), such that adjusting knob (82) will simply "freewheel" without rotating threaded sleeve (304) whenever adjusting knob (82) is rotated with safety latch (88) positioned to unlock staple actuating lever (86). Other suitable variations will be apparent to those of ordinary skill in the art having the benefit of the teachings herein.

While the examples herein are described mainly in the context of surgical anastomosis stapling instruments, it should be understood that the teachings herein may be readily applied to a variety of other types of medical instruments. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument comprising:
   (a) an anvil assembly;
   (b) a stapling head assembly, wherein the stapling head assembly is operable to drive a plurality of staples toward the anvil assembly, and wherein the anvil assembly is movable relative to the stapling head assembly;
   (c) an actuator assembly, comprising:
      (i) a first actuator operable to control motion of said anvil assembly relative to the stapling head assembly, and
      (ii) a second actuator operable to actuate the stapling head assembly to thereby drive the plurality of staples toward the anvil assembly;
   (d) a safety feature responsive to said first actuator, wherein the safety feature comprises a pivoting member, wherein the safety feature is configured to prevent operation of said second actuator when a gap between the anvil assembly and the stapling head assembly is outside a predetermined distance, wherein the pivoting member is operable to pivot when the gap is within the predetermined distance, wherein the pivoting member is not operable to pivot when the gap is outside the predetermined distance; and
   (e) a locking member responsive to said safety feature, wherein the locking member is configured to prevent operation of said first actuator in response to pivoting of the pivoting member.

2. The instrument of claim 1, wherein the locking member is integral to the safety feature.

3. The instrument of claim 2, wherein the first actuator comprises an adjusting knob that is rotatable to control motion of said anvil assembly; and
   wherein the safety feature further comprises an integral arm that is configured to selectively prevent rotation of the adjusting knob when the safety feature is positioned to allow operation of the second actuator.

4. The instrument of claim 3, wherein the safety feature includes a plurality of arms.

5. The instrument of claim 3, wherein the first actuator further comprises an extension feature unitarily coupled with the adjusting knob, wherein the extension feature has a plurality of flat sides, wherein the integral arm of the safety feature is operable to selectively engage either or both of the knob or at least one flat side of the plurality of flat sides.

6. The instrument of claim 5, wherein the plurality of flat sides together define a polygonal cross section.

7. The instrument of claim 3, wherein the integral arm is movable from a first position to a second position, wherein the integral arm is substantially parallel with a rotational axis of the adjusting knob when the integral arm is in the first position, wherein the integral arm is oriented obliquely relative to the rotational axis of the adjusting knob when the integral arm is in the second position.

8. The instrument of claim 3, wherein the first actuator further comprises a threaded sleeve unitarily secured to the adjusting knob and a control rod having a threaded section engaged with the threaded sleeve such that the adjusting knob is rotatable to translate the control rod via the threaded sleeve.

9. The instrument of claim 1, wherein the locking member is movable longitudinally to prevent operation of the first actuator when the safety feature is positioned to allow operation of the second actuator.

10. The instrument of claim 9, wherein the first actuator comprises an adjusting knob that is rotatable to control the motion of said anvil assembly;
    wherein the adjusting knob includes at least one tooth; and
    wherein the locking member includes a plurality of teeth operable to selectively engage the at least one tooth of the adjusting knob to prevent rotation of the adjusting knob when the safety feature is positioned to allow operation of the second actuator.

11. The instrument of claim 10, wherein the locking member comprises a body that is configured to enclose a portion of the adjusting knob when the safety feature is positioned to allow operation of the second actuator.

12. The instrument of claim 11, wherein the body comprises a cylinder.

13. The instrument of claim 9, wherein the first actuator comprises an adjusting knob that is rotatable to control the motion of said anvil assembly; and
    wherein the locking member includes a linkage that is configured to engage the adjusting knob to prevent rotation of the adjusting knob when the safety feature is positioned to allow operation of the second actuator.

14. The instrument of claim 13, wherein the adjusting knob further comprises a plurality of teeth.

15. The instrument of claim 14, wherein the linkage comprises a hook operable to selectively engage the teeth of the adjusting knob when the safety feature is positioned to allow operation of the second actuator.

16. The instrument of claim 14, wherein the linkage comprises a wedge operable to selectively engage the teeth of the adjusting knob when the safety feature is positioned to allow operation of the second actuator.

17. The instrument of claim 13, wherein the linkage comprises a friction brake that is operable to selectively engage the adjusting knob when the safety feature is positioned to allow operation of the second actuator.

18. The instrument of claim 1, wherein the stapling head assembly is operable to drive the plurality of staples in a generally circular array.

19. An instrument comprising:
(a) an anvil assembly;
(b) a stapling head assembly, wherein the stapling head assembly is operable to drive a plurality of staples toward the anvil assembly, and wherein the anvil assembly is movable relative to the stapling head assembly;
(c) an actuator assembly, comprising:
 (i) a first actuator operable to control motion of said anvil assembly relative to the stapling head assembly, and
 (ii) a second actuator operable to actuate the stapling head assembly to thereby drive the plurality of staples toward the anvil assembly;
(d) a safety feature responsive to said first actuator, wherein the safety features comprises a pivotable member, wherein the safety feature is configured to prevent operation of said second actuator when a gap between an element of the anvil assembly and an element of the stapling head assembly is outside a predetermined gap distance, wherein the pivotable member is operable to pivot when the gap is within the predetermined gap distance, wherein the pivotable member is not operable to pivot when the gap is outside the predetermine gap distance; and
(e) a locking member responsive to said safety feature, wherein the locking member is configured to transition from a non-locking state to a locking state in response to pivotal movement of the pivotable member, wherein the locking member is configured to prevent operation of said first actuator in the locking state.

20. A method of operating an instrument comprising:
(a) actuating a first actuator to move an anvil assembly toward a stapling head assembly to a set distance between the anvil assembly and the stapling head assembly, wherein the stapling head assembly is configured to hold a plurality of staples;
(b) pivoting a safety feature when a gap between the anvil assembly and the stapling head assembly is at the set distance, to enable operation of a second actuator operable to actuate the stapling head assembly to thereby drive the plurality of staples toward the anvil assembly;
(c) driving a locking feature via pivoting of the safety feature in order to lock movement of the first actuator in response to the safety feature being moved to allow operation of the second actuator; and
(d) actuating said second actuator to drive the staples from the stapling head assembly against said anvil assembly.

* * * * *